(12) United States Patent
Chen et al.

(10) Patent No.: US 9,518,952 B2
(45) Date of Patent: *Dec. 13, 2016

(54) GAS SENSOR

(75) Inventors: Lei Chen, South Windsor, CT (US); Zhiwei Yang, South Windsor, CT (US); Jean Yamanis, South Glastonbury, CT (US); Georgios S. Zafiris, Glastonbury, CT (US); Joseph J. Sangiovanni, West Suffield, CT (US)

(73) Assignee: UTC FIRE & SECURITY CORPORATION, Farmington, CT (US)

( * ) Notice: Subject to any disclaimer, the term of this patent is extended or adjusted under 35 U.S.C. 154(b) by 166 days.

This patent is subject to a terminal disclaimer.

(21) Appl. No.: 14/349,905

(22) PCT Filed: Oct. 5, 2011

(86) PCT No.: PCT/US2011/054855
§ 371 (c)(1),
(2), (4) Date: Apr. 4, 2014

(87) PCT Pub. No.: WO2013/052041
PCT Pub. Date: Apr. 11, 2013

(65) Prior Publication Data
US 2014/0251834 A1    Sep. 11, 2014

(51) Int. Cl.
G01N 27/403    (2006.01)
G01N 27/407    (2006.01)
G01N 27/40    (2006.01)
G01N 27/413    (2006.01)

(52) U.S. Cl.
CPC ............ G01N 27/407 (2013.01); G01N 27/40 (2013.01); G01N 27/4074 (2013.01); *G01N 27/413* (2013.01)

(58) Field of Classification Search
CPC .......................... G01N 27/403; G01N 27/413
See application file for complete search history.

(56) References Cited

U.S. PATENT DOCUMENTS

| | | |
|---|---|---|
| 5,573,648 A | 11/1996 | Shen et al. |
| 5,650,054 A | 7/1997 | Shen et al. |
| 6,200,443 B1 | 3/2001 | Shen et al. |
| 6,948,352 B2 | 9/2005 | Rabbett et al. |
| 7,279,080 B2 | 10/2007 | Chapples et al. |
| 8,840,775 B2 * | 9/2014 | Chen .................. G01N 27/4045 204/431 |

(Continued)

FOREIGN PATENT DOCUMENTS

| | | | | |
|---|---|---|---|---|
| GB | 2395564 A | * | 5/2004 | ............. G01N 27/28 |
| JP | 2006-98269 A | * | 4/2006 | ............. G01N 27/30 |
| KR | 20080050951 A | | 6/2008 | |

OTHER PUBLICATIONS

JPO computer-generated English language translation of Inoue et al. JP 2006-98269 A. Downloaded Dec. 12, 2015.*

(Continued)

*Primary Examiner* — Alexander Noguerola
(74) *Attorney, Agent, or Firm* — Cantor Colburn LLP

(57) ABSTRACT

A membrane electrode assembly for a gas sensor is described that includes a membrane disposed between a sensing electrode and a counter electrode. The membrane is a polymer membrane, such as an ionomer, having an ionic liquid retained therein.

20 Claims, 5 Drawing Sheets

(56) References Cited

U.S. PATENT DOCUMENTS

2006/0234113 A1 10/2006 Rohrl
2008/0128285 A1 6/2008 Moon et al.
2010/0133120 A1 6/2010 Varney et al.
2011/0048943 A1 3/2011 Nemes

OTHER PUBLICATIONS

Yasuda, Ayumu, et al., "Electrochemical carbon monoxide sensor with a Nafion film", Reactive & Functional Polymers, 1999, pp. 235-243, vol. 41, Elsevier.
Yasuda, Ayumu, et al., "Mechanism of the Sensitivity of the Planar CO Sensor and Its Dependency on Humidity", J. Electrochem. Soc., Nov., 1992, pp. 3224-3229, vol. 139, No. 11.
Bennett, Mathew D., et al., "Ionic Liquid as Stable Solvents for Ionic Polymer Transducers", Sensors and Actuators A, 2004, pp. 79-90, vol. 115.
International Search Report for International Application No. PCT/US2011/054855 mailed Jul. 27, 2012, 3 pages.
Written Opinion for International Application No. PCT/US2011/054855 mailed Jul. 27, 2012, 4 pages.
Wang, Rong, et al., "A Novel Amperometric O2 Gas Sensor Based on Supported Room-Temperature Ionic Liquid Porous Polyethylene Membrane-Coated Electrodes", Electroanalysis 2004, vol. 16, No. 1-2, pp. 66-72. Wiley-VCH, Verlag GmbH & Co. KGaA, Weinheim.

* cited by examiner

GAS SENSOR

BACKGROUND OF THE INVENTION

Electrochemical gas sensors are widely used for sensing a variety of different gases. Although the specific design features of these sensors can vary widely based on the electrochemical reactions of the gas species being sensed, the environments in which the sensors are used, and other factors, the sensors generally share common features, such as having two electrodes (an anode and a cathode) separated by an electrolyte. One type of sensor in wide use today is the carbon monoxide sensor. Carbon monoxide sensors generally utilize an anode as a sensing electrode (exposed to air being tested for the presence of CO) and a cathode as a sealed reference electrode that is exposed to clean air, separated by an electrolyte. The reaction that takes place at the sensing electrode (anode) is set forth as $CO+H_2O \rightarrow CO_2+2H^++2e^-$. The protons liberated by the reaction taking place at the anode are transferred through the electrolyte to the cathode, where they participate in the reaction $\frac{1}{2}O_2+2H^++2e^- \rightarrow H_2O$. The electrons liberated at the anode are conducted to the cathode through a monitored circuit that measures current and/or voltage, with the current/voltage in this circuit being proportional to the concentration of CO in the gas being tested. As can be readily seen by combining these chemical equations, the net reaction of the electrode assembly results in no net production or consumption of water or electrolyte components.

Some designs of carbon monoxide sensors utilized liquid electrolytes such as aqueous sulfuric acid. Such electrolytes, however, are subject to leakage of electrolyte from the sensor assembly, which can expose the surrounding environment to corrosive chemicals, as well as result in degraded performance or failure of the sensor due to electrolyte dry-out. Evaporation of water from such aqueous liquid electrolytes can also result in degraded performance or failure of the sensor. Sensors with such liquid electrolytes can often be utilized only in limited operating environments in terms of temperature and humidity, and also have to include complex design features to isolate the liquid electrolyte from the outside environment. Other designs of carbon monoxide sensors (see, e.g., U.S. Pat. No. 5,573,648) propose using solid electrolyte like the ionomer Nafion®, manufactured by the E.I. du Pont de Nemours and Company. An electrode assembly with such a solid electrolytes is known as a membrane electrode assembly ("MEA"). Such ionomeric electrolytes require the presence of water vapor in order to provide the desired electrolyte performance for gas sensors, and sensor designs that use such ionomeric solid electrolytes typically must have a water reservoir integrated with the sensor in order to maintain humidity levels in the ionomeric solid electrolyte (see, e.g., U.S. Pat. Nos. 6,200,443 and/or 6,948,352). The necessity of a water reservoir adds cost, size, and complexity to the overall sensor design, as well as providing a failure mode for the sensor if the reservoir seal is compromised. Also, since a gas sensor cannot be completely sealed since it must be open at least to the gas being tested, the water reservoir is subject to evaporation and thus has a finite life, which can be further shortened if the sensor is operated in dry and warm environments.

In view of the sometimes demanding requirements for gas sensor electrolytes, various alternatives have been used or proposed. However, new alternatives are always well-received that may be more appropriate for or function better in certain environments, offer better cost, or enable beneficial modifications to the overall sensor design.

BRIEF DESCRIPTION OF THE INVENTION

According to an exemplary embodiment, a membrane electrode assembly for a gas sensor includes a sensing electrode, a counter electrode, and a polymer membrane disposed between the sensing electrode and the counter electrode, the polymer membrane comprising an ionic liquid retained therein. In an exemplary embodiment, the polymer of the polymer membrane and electrodes is a proton conducting ionomer. In another exemplary embodiment, the membrane includes a polymer matrix and a proton-conducting ionic liquid retained in the matrix. In yet another exemplary embodiment, the membrane includes a proton-conducting ionomer matrix and a proton-conducting ionic liquid retained in the matrix. In still another exemplary embodiment, the membrane includes a proton-conducting ionic liquid molecule or moiety grafted to a polymer repeat unit or matrix.

In another exemplary embodiment, the electrodes can be formed from a proton-conducting matrix with or without a proton-conducting ionic liquid retained in the matrix. In yet another exemplary embodiment, the electrodes include a proton-conducting ionic liquid grafted polymer. The electrodes and membrane can include different proton-conducting ionic liquids or different ionic liquid grafted polymers.

In another exemplary embodiment, the membrane electrode assembly, or MEA, is used in a gas sensor, including but not limited to a carbon monoxide sensor. In a further exemplary embodiment, the MEA is used in a carbon monoxide sensor that is free of a water reservoir. The sensor can be operated by generating a difference in electrochemical potential between the sensing electrode and the counter electrode that is responsive to the presence and/or concentration of a gas being tested, measuring voltage or current between the sensing electrode and the counter electrode by an electrical circuit while the sensing and counter electrodes are held at a fixed potential (potentiostatic mode), and converting the measured voltage or current to a reading indicative of the presence and/or concentration of the gas being tested. In a further exemplary embodiment, the method of operating the sensor includes adjusting the conversion of measured voltage or current to the reading indicative of the presence and/or concentration of the gas being tested, based on the humidity of the environment, which may be determined by measuring the impedance or conductivity of the MEA.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

DETAILED DESCRIPTION OF THE INVENTION

Figure 1:
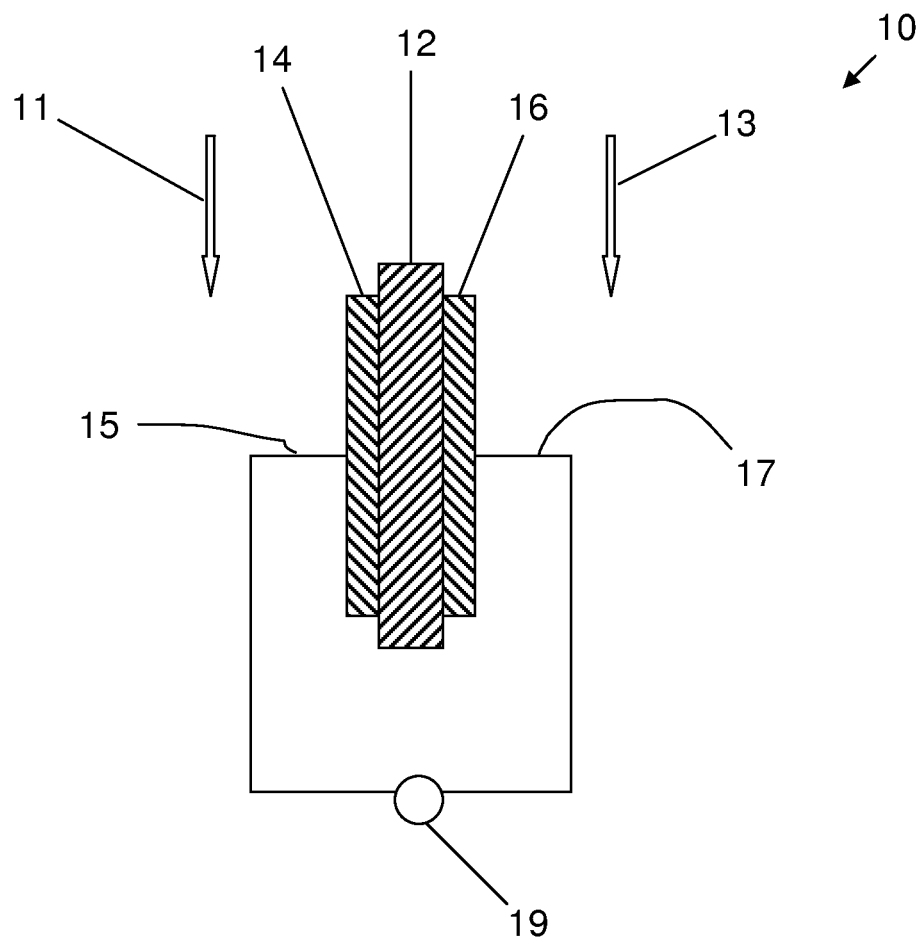
FIG. 1 depicts a simplified schematic representation of an MEA for a gas sensor.

A simplified MEA is schematically shown in FIG. 1, in which a membrane electrode assembly 10 has a polymer membrane 12 with an ionic liquid retained therein disposed between sensing electrode 14 and counter electrode 16. Current collectors 15 and 17 are attached to the electrodes and complete a circuit between the electrodes having a voltmeter or ampere meter 19 disposed therein. The electrodes are exposed to test gas 11 and reference gas 13, which generates an electrical current in the circuit, which can be read by voltmeter or ammeter 19 or electronic signal processing circuitry with similar functionalities.

Figure 2:
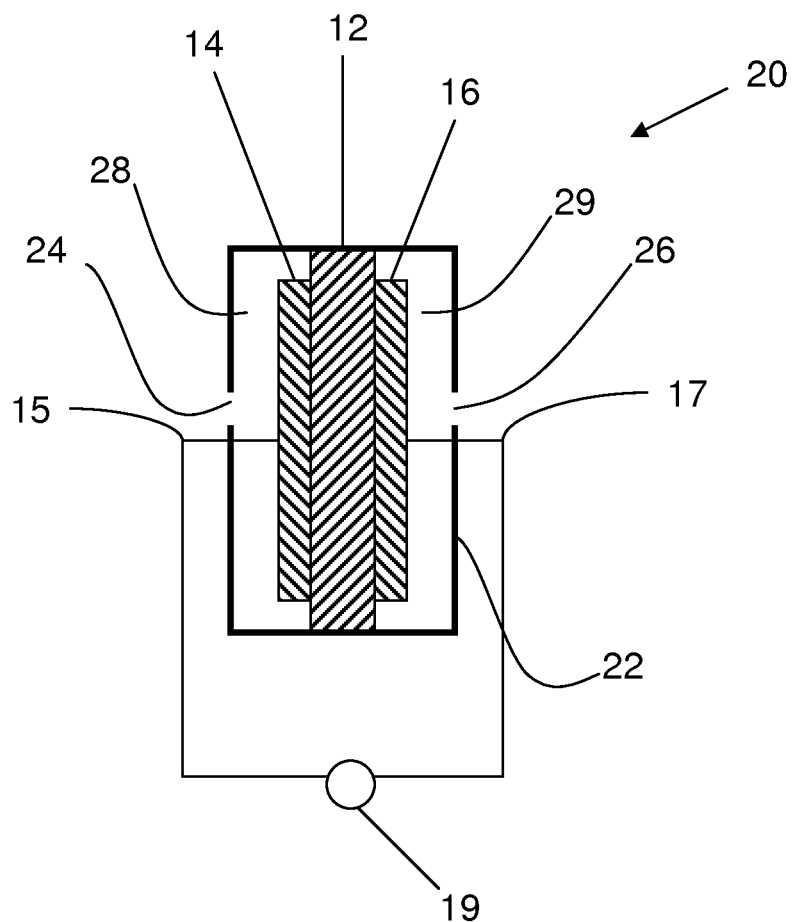
FIG. 2 depicts a simplified schematic representation of a gas sensor utilizing the MEA of FIG. 1.

The MEA described herein may be incorporated into a gas sensor, which may typically also include a housing, seals, one or more channels or wicking elements to guide test and/or reference gases to the electrodes, electrical connections and wiring (i.e., current collectors). These sensors measure current or voltage generated by the electrochemical reaction(s) utilized in sensing component(s) in the gas being tested, connectors, output displays, and the like. Such sensors and variations in their configurations are disclosed, for example, in U.S. Pat. Nos. 5,650,054, 5,573,648, 6,200,443, and 6,948,352, the disclosures of which are incorporated herein by reference in their entirety. Unlike some known sensors, the electrode assemblies described herein do not require a water reservoir (and the associated channels or other configuration utilized to deliver water vapor from the reservoir to the MEA), although they may utilize a water reservoir as an optional component. Another simplified schematic drawing of a typical gas sensor is shown in FIG. 2, which depicts a gas sensor 20 having the MEA 10 from FIG. 1 disposed in housing 22 having opening 24 for circulation of a test gas and opening 26 for circulation of a reference gas. The openings are shown as completely open, although it is understood that they may be covered with a screen or gas permeable membrane. Also, the openings are shown for purposes of illustration as leading directly into chambers 28 and 29 for the test gas and the reference gas, respectively, but the gases may also be introduced into interior chambers through channel(s) that lead from an outer surface of the sensor to interior chambers. Also, although FIG. 2 provides an opening 26 for reference gas to enter the reference gas chamber, in certain embodiments the reference gas chamber 29 can be sealed. For example, a carbon monoxide sensor only uses up minute amounts of reference oxygen in the rare instances when carbon monoxide is present at the sensing electrode, allowing for the reference gas chamber 29 to be sealed. The edges of the electrode assembly membrane 12 are sealed against the inner surface of housing 22 so that the test gas and reference gas are maintained on opposing sides of the MEA, although other techniques known in the art (e.g., disposing the MEA in a frame (not shown) that is sealed to the edges of the housing) can be used. Although the electrodes are shown to be bonded to the electrolyte/membrane in these figures, the entity including two electrodes and a separator membrane also can be mechanically clamped together without compromising the functionalities of the sensor.

Figure 3:
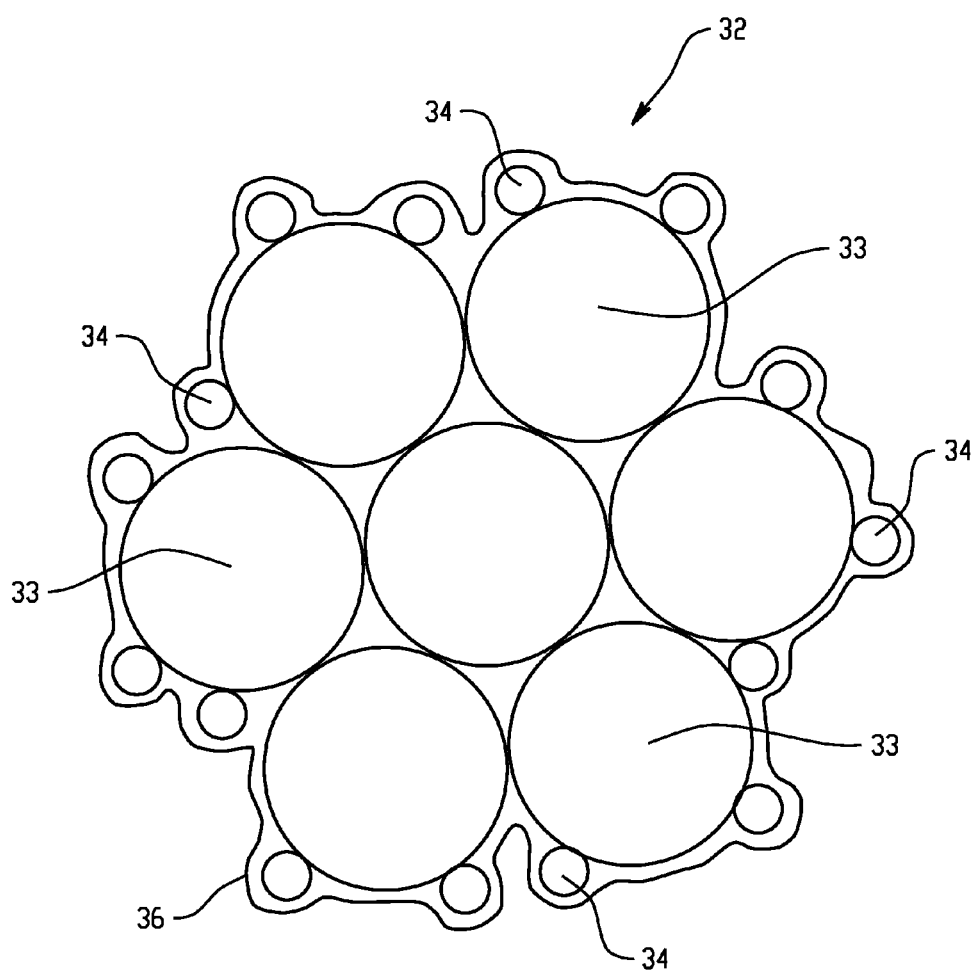
FIG. 3 depicts a schematic representation of an ionomer-covered carbon-supported catalyst agglomerate useful for forming the sensing (anode) and counter (cathode) electrodes of an MEA for a gas sensor.

The precise composition of the electrodes, and materials used in fabricating them, will depend on the particular electrochemistry involved for the gas being tested. Similarly, the physical configuration of the electrodes will depend on the size and shape of the sensor. For electrochemical reactions that produce low amounts of current, thin electrodes can be utilized to reduce internal ionic resistance, with electrode thicknesses of 1 to 20 μm being useful in an exemplary embodiment of a CO sensor. A variety of metals and alloys (e.g., iridium, rhenium, palladium, platinum, copper, indium, rubidium, silver, gold) alone or supported on electrically conductive carbon may be used in conjunction with a proton-conducting ionomer to form the electrodes. Supported or non-supported catalysts are disposed in both the sensing and the counter electrode to allow tunable sensor performance. In an exemplary embodiment of a carbon monoxide sensor, and also in some other types of sensors, the electrodes may be formed from an agglomerate of carbon, catalytic platinum, and a binder such as a proton-conducting ionomer, as shown in FIG. 3. FIG. 3 depicts a portion of a carbon agglomerate 32 having carbon particles 33 with a nominal diameter of about 40 nm, with platinum particles 34 (nominal diameter of about 4 nm) disposed thereon, covered by a thin layer of ionomer 36 such as Nafion®. In an exemplary embodiment, the electrode may also contain an ionic liquid retained (as described below with respect to the polymer membrane) by the ionomer, carbon supported catalyst particles (if present), or both. Electrodes may be deposited (e.g., by screen printing, inkjet printing, metal vapor deposition, casting, or other deposition techniques depending on the composition and characteristics of the electrode) onto a pre-formed electrolyte, or an electrode may be formed first followed by deposition of the electrolyte and then another electrode.

In exemplary embodiments as described herein, the electrolyte for an MEA for a gas sensor is provided by a membrane between the sensing electrode and the reference electrode. This membrane includes an ionic liquid retained therein. Ionic liquids are generally recognized in the scientific literature as being salts having a melting point below 100° C.; however, the melting point for ionic liquids useful in the exemplary embodiments described herein can vary depending on the anticipated operating temperatures of the gas sensor, and could even be higher than 100° C. for high-temperature applications. In exemplary embodiments for sensors to be used in normal ambient conditions, ionic liquids having a melting point below 0° C. will provide performance at temperatures at least as low as the freezing point of water. Many ionic liquids offer high electrochemical stability (e.g., up to roughly 6 V vs. Standard Hydrogen Electrode (SHE), compared to 1.23V vs. SHE for water) and/or high conductivity (>1 mS/cm, and up to 100 mS/cm under ambient temperature). The electrochemical stability and conductivity of ionic liquids used in the electrode assemblies described herein can vary significantly depending on the characteristics and requirements of the electrochemical reactions involved with sensing the gas in question. In one exemplary embodiment, an ionic liquids used in these electrode assemblies can have electrochemical stability of from 0 V to 6 V (vs. SHE), more specifically, from 0 to 4.5 V (vs. SHE), and/or a conductivity between 1 mS/cm and 100 mS/cm.

Ionic liquids are well-known, and have been the subject of significant study and research. Ionic liquids tend to be air and water stable. Exemplary cations for ionic liquids used in the embodiments described herein include, but are not limited to imidazolium (e.g., 1-ethyl-3-methylimidazolium, 1-ethyl-2,3-dimethylimidazolium, 1-butyl-3-methylimidazolium ("BMI"), 1-hexyl-3-methyl-imidazolium ("HMI"), pyridinium (e.g., N-methylpyridinium), tetraalkylammonium, pyrrolidinium (e. g., 1-butyl-1-methyl-pyrrolidinium ("BMPyr"), trialkylsulfonium (e.g., triethylsulfonium), pyrazolium, triazolium, thiazolium, oxazolium, pyridazinium, pyrimidinium, pyrazinium. Exemplary anions for ionic liquids used in the embodiments described herein include, but are not limited to, tetrafluoroborate ($BF_4$), hexafluorophosphate ($PF_6$), trifluoromethanesulfonate ($CF_3SO_3$), trifluoroethanoate, nitrate, SCN, $HSO_4$, $HCO_3$, $CH_3SO_3$, $CH_3CH_2SO_4$, $(CH_3(CH_2)_3O)_2POO$, $(CF_3SO_2)2N$, dicyanamide, $(CF_3CF_2SO_2)_2N$, L-(+)-lactate, $CH_3SO_4$, and $CH_3COO$, and the like.

In one exemplary embodiment, the ionic liquid has a cation that is an imidazolium, and more specifically the ionic liquid has the formula:

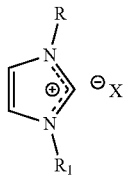

wherein, R and $R_1$ are independently selected from H, an unsubstituted or substituted alkyl group having 1 to 30 carbon atoms, or an unsubstituted or substituted aryl group having 6 to 30 carbon atoms. $X^\ominus$ is an anionic group, as described hereinabove, that associates with imidazolium to form an ionic-liquid cation/anion pair.

As described herein, the ionic liquid is retained in a polymer membrane disposed between two electrodes. The term "retained" is not meant to require absolute retention where it would be impossible for even minute quantities of the ionic liquid to migrate out of the polymer membrane, but rather substantial retention such that ionic liquid is present to impact the ionic characteristics of the polymer membrane. Retention of the ionic liquid in the membrane may be achieved, for example, by including a polymer matrix in the membrane having porosity characteristics such that ionic liquid can be retained within pores, cells, or other interstitial spaces in the polymer matrix. The term matrix includes any configuration of polymer segments and interstitial space between polymer segments that is available for occupation by the molecules and/or atoms of the ionic liquid atoms/molecules, and is not limited to any particular type of regular or irregular configuration. The scale of interspersed polymer segments and ionic liquid can be from angstrom to sub-micrometer, with ionic liquid molecules and/or atoms interspersed with polymer chain molecules and retained in the matrix by physical adsorption, molecular entanglements, or the ionic liquid can be retained in larger polymer segments and structures such as mesoporous polymer structures or microcellular polymer foam structures. Ionic liquids can be integrated with the polymer matrix using various known techniques, including but not limited to forming a solution that includes a polymer and an ionic liquid and casting a film from the solution, diffusing an ionic liquid into a pre-formed polymer membrane structure (e.g., by dipping or soaking), or melt-blending a polymer with an ionic liquid and casting or extruding a film from the blended melt or other polymer membrane forming techniques known in the art.

Ionic liquid molecules can also be chemically retained in the polymer membrane by grafted with the polymer. In one exemplary embodiment, an imidazolium is attached as a pendant group on a polymer backbone. For example, an imidazolium can be covalently tethered as a pendant group on a polymer's backbone (such as polyethylene, ref: U.S. Pat. No. 7,897,661) or a polymer's side chain (such as on the phenyl ring of polystyrene, ref: Langmuir 2004, 20, 596-605). In another exemplary embodiment, an imidazolium is incorporated into a polymer backbone. For example, an imidazolium can be inserted into a polyethylene backbone (ref: *Anal. Methods*, 2010, 2, 455-457) or a polyoxyalkylene ester backbone (ref: *Journal of Membrane Science*, 2011, 1-2, 1-4) to form main-chain imidazolium polymers. An anionic group (such as its corresponding H+ form acid, $X^\ominus$-$H^\oplus$), which can associate with imidazolium, can be directly added into imidazolium-containing polymer, or tethered on the same or different polymers and then mix, either intramolecular (the former cases) or intermolecular (the latter cases), with imidazolium to form an ionic-liquid cation/anion pair, see *Nature Materials*, 2009, 8, 621.

The amount of ionic liquid in the polymer membrane can vary depending on the parameters and desired performance of the MEA. For an ion conducting polymer such as Nafion, where ionic conductivity is dependent primarily on the side chain function groups, i.e, sulfonic groups ($SO_3^-$), its conductivity is determined by the density of those functional groups represented by equivalent weight (EW) (mass of dry Nafion per mole of sulfonic acid groups) and water content $\lambda$ given as $\lambda=(W_{H2O}$(g water/gram Nafion)$\times EW/M_{H2O}$). As an example, when water molecules are replaced by ionic liquids, the amount of ionic liquids can be represented by $\lambda$ as well, i.e., $\lambda=(W_{IL}$(g IL/gram Nafion)$\times EW/M_{IL}$). In an exemplary embodiment, the $\lambda$ of membrane with ionic liquids ranges from 0.1 to 5. The thickness of the membrane can also vary depending on the parameters and desired performance of the MEA. In an exemplary embodiment, the membrane has a thickness ranging from 1 micron to 500 micron, more specifically from 5 micron to 100 micron.

Exemplary polymers for the polymer membrane described herein can include any polymer capable of forming a matrix structure that is able to retain the ionic liquid. For larger matrix structures like mesoporous or microcellular structures, the polymer should form a structure having surface characteristics as well as porosity or cellular characteristics that allow the structure to retain the ionic liquid, and virtually any polymer capable of forming such structures may be used, including but not limited to polyesters (including polyoxyalkylene esters), polyolefins, polyurethanes, acrylic polymers, polyimide, polysulfone, polyarylsulfone, polybenzimidazole ("PBI"), co-polymers (e.g., poly-arylene-ether-sulfone co-polymers or block-copolymers), polyetherimide-siloxane copolymers, perfluorinated polymers (e.g., polytetrafluoroethylene ("PTFE"), and perfluoroalkoxy copolymer ("PFA")), and partially fluorinated polymers (e.g., polyvinylidene fluoride ("PVDF")). The type of polymer molecular structure can be important in selection of a polymer to retain an ionic liquid in a nano-scale polymer matrix. The polymer may be non-ionic or it may be ionic (e.g., DuPont Nafion® ionomer). Useful non-ionic polymers for retaining the ionic liquid on such a scale include but are not limited to polyoxyalkylene (i.e. polyoxyethylene), per- or partially fluorinated polymers (i.e. PFA, PTFE, PVDF), polystyrene, heteroaromatic polymers (such as polyaniline, polypyrrole, PBI). Useful ionic polymers may include ionic groups attached to a polymer so that the polymer has the ionic-exchange ability, such groups including but not limited to sulfonic acid, phosphonic acid, and sulfonimide acid. Exemplary ionomers include perfluorinated sulfonic acid ("PFSA"), such as Nafion® ionomer and Solvey Solexis Augivion™ ionomer, sulfonated polystyrene, sulfonated polysulfon, disulfonated poly(arylene ether sulfone) block-copolymers ("BPSH"). Conventional additives, e.g., surfactants, solvents (e.g., polyethylene glycol), and fine particles (such as functionalized of non-functionalized silica, carbon-based powders, metal-oxides particles) may also be added to the polymer matrix.

The electrode assemblies described herein are useful in gas sensors, the configurations of which can vary widely, and are well-known in the art. The MEA can function in environments of low or no humidity, and therefore the provision of a source of water vapor to the polymer membrane is optional, and in some embodiments the sensor is free of any water reservoir. In some embodiments, a water reservoir or other source of water vapor to the membrane may be useful. For example, humidity can impact the sensitivity of sensors utilizing exemplary embodiments of the electrode assemblies described herein, and providing a source of water vapor can provide a desired sensitivity.

In some embodiments, the sensor is a carbon monoxide sensor where the polymer membrane with ionic liquid functions as a proton exchange membrane, as described hereinabove. Such sensors can be operated by exposing the sensing electrode to the gas being sensed to generate a difference in electronegative potential between the sensing electrode and the reference electrode that is responsive to the presence and/or concentration of a component in a gas being tested, measuring voltage or current in an electrical circuit connecting the sensing electrode and the counter electrode, and converting the measured voltage or current to a reading indicative of the presence and/or concentration of the component in the gas being tested. Some exemplary embodiments of the sensors described herein (e.g., exemplary embodiments utilizing an acid salt anionic group-containing ionomer) may exhibit variations in sensitivity base on the humidity of the environment. Accordingly, in some exemplary embodiments, an algorithm for converting the measured voltage or current from the MEA can include functionality for adjusting the conversion based on the humidity of the environment, which can be determined based on the impedance or conductivity of the membrane using DC or AC impedance techniques. The impedance can be measured by applying an AC excitation with or without a DC bias at one or more frequencies (10-10000 Hz for example). This period is much shorter than CO detection time and the impedance measurement can be carried out while CO is being detected or when no CO is measured.

The compositions and their use are further described below in the following non-limiting examples.

EXAMPLES

Preparation of an electrode composition for an MEA as described herein included: in a $N_2$-protected glove box, Pt/carbon catalyst (TEC10E50E, 46.7% Pt on Ketjen black carbon, Tanaka Kikinzoku Kogyo KK, Japan) and ionic liquids were dispersed in isopropyl alcohol/D.I. water (60:40 volume ratio) mixture solvents. Nafion® dispersion (5-6 wt %, 1100 equivalent weight; Dupont Fluoroproducts, Wilmington, Del.) was added to form catalyst-ionomer ink with the catalyst/Nafion weight ratio of ~80/20. The resultant ink was screen printed on a Teflon® film (127 micro thickness) to form decals, which had Pt loading of $0.1\pm0.01$ mg-Pt/cm$^2$. The ink-coated decals were dried in a $N_2$ protected chamber at room temperature and 30% relative humidity for overnight. The dried decals were then hot-pressed at once onto both sides of Nafion®-112 membranes ($H^+$ form, purchased from Aldrich) under 130° C., 450 Psi for 5 minutes.

Another MEA preparation method is to cast electrodes directly onto a membrane followed by hot pressing to form the MEA without screen printing process. Pt catalyst (99.9% purity, fuel cell grade, Johnson Matthey) was dispersed in isopropyl alcohol/D.I. water (60:40 volume ratio) mixture solvents in a $N_2$-protected glove box. Nafion® dispersion (5-6 wt %, 1100 equivalent weight; Dupont Fluoroproducts, Wilmington, Del.) was added to form catalyst-ionomer ink with the catalyst/Nafion weight ratio of 90-95/10-5. The resultant ink was dried with $N_2$ purging and stirring. The resultant dry particle was grinded through 300 stainless steel mesh to give fine powder. The fine powder along with an ionic liquid was ultrasonically dispersed in hexane and immediately cast on one side of a Nafion®-112 membrane ($H^+$ form, Aldrich), followed by air-drying and by hot-pressing under 130° C., 450 Psi for 5 minutes to give a uniform coating with Pt loading of $0.4\pm0.04$ mg-Pt/cm$^2$ on the Nafion®-112 membrane. The above steps were repeated to cast the grinded fine powder catalyst on the other side of the Nafion®-112 membrane to form a complete MEA. Before the hot-pressing, the Nafion®-112 membranes were impregnated with either BMI-BF$_4$ or HMI-FAP ionic liquid by soaking at an elevated temperature up to 100° C. The resultant MEA was sandwiched between 2 pieces of carbon paper with a micro-porous layer (SGL-25BC, SGL Carbon Group, Germany) as gas diffusion media as well as current collectors at the same time.

The MEA was disposed and sealed in a housing such that the counter (cathode) electrode was exposed to a sealed chamber with clean air therein, while the sensing electrode was exposed to a sealed chamber having an aperture for introducing test gas. Gas diffusion layers with cleaning agent such as a activated carbon bag were also placed in the passage to the sensing electrode. The current collectors were connected through a circuit having a potentiostat, which was set to hold the potential constant at the level associated with the uncontaminated state and measure current as the sensing electrode was exposed at various relative humidity levels to gas test samples introduced through the aperture. The measured results are shown in FIGS. 4-6.

Figure 4:
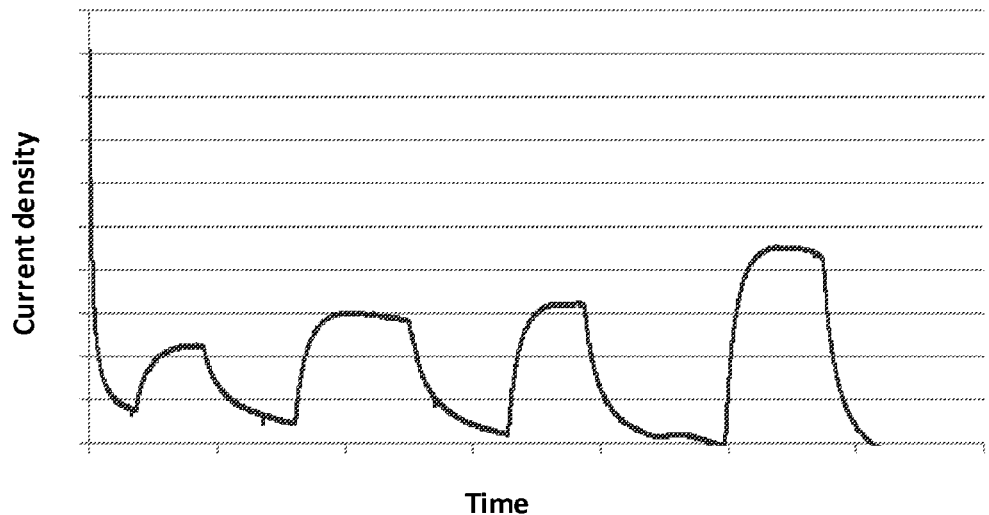
FIG. 4 is a plot of surface area-normalized current produced by an exemplary gas sensor in response to exposure to CO-containing gas.
Figure 5:
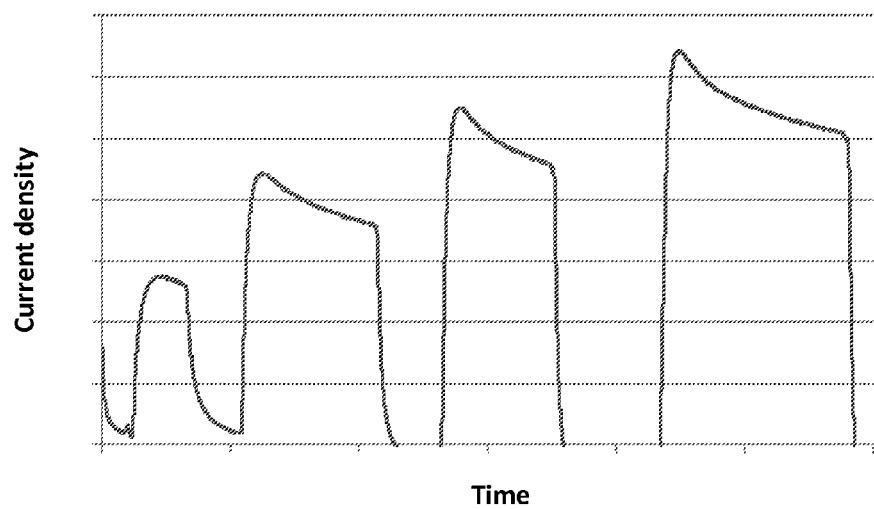
FIG. 5 is a plot of surface area-normalized current produced by another exemplary gas sensor in response to exposure to CO-containing gas.
Figure 6:
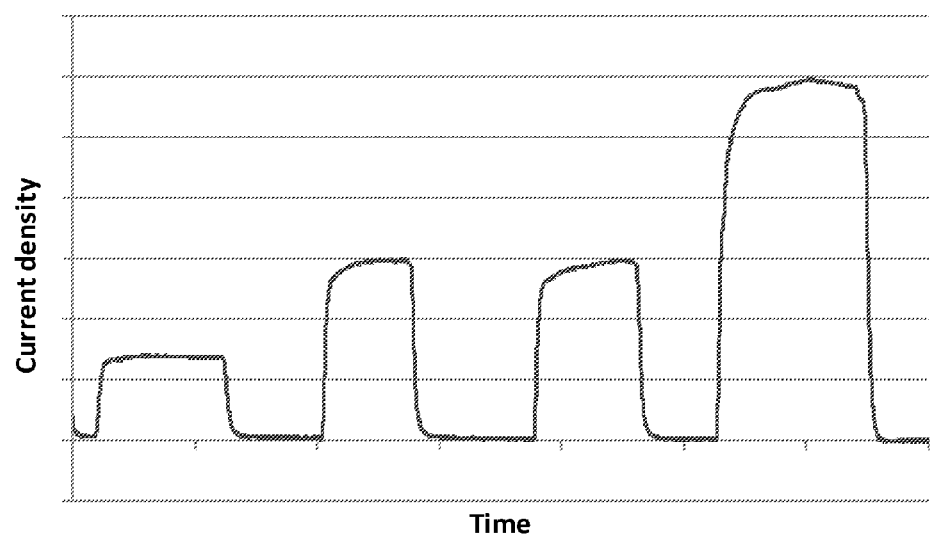
FIG. 6 is a plot of surface area-normalized current produced by an exemplary gas sensor in response to exposure to CO-containing gas.

FIGS. 4-6 depict plots of sensor response (current density) versus time as different CO-containing samples were introduced through the aperture of the sensor with the membrane impregnated with BMI-BF$_4$, with FIG. 4 representing 0% relative humidity, FIG. 5 representing 33% relative humidity, and FIG. 6 representing 100% relative humidity. FIG. 4 shows clear peaks for CO samples at 49 ppm, 100 ppm, 157 ppm, and 217 ppm, operating under completely dry conditions. FIGS. 5 and 6 show similar results, with sensitivity increasing significantly as relative humidity increased. These results show clear peaks for various CO concentrations, demonstrating less sensitivity to humidity for the sensor with the HMI-FAP-impregnated membrane than the sensor with the BMI-BF$_4$-impregnated membrane, perhaps due to its greater hydrophobicity and differences in CO transport properties.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A membrane electrode assembly for a gas sensor, comprising:
   a sensing electrode;
   a counter electrode; and
   a polymer membrane comprising an ionomer, disposed between the sensing electrode and the counter electrode, the polymer membrane comprising an ionic liquid retained therein.

2. The assembly of claim 1, wherein the ionomer has a molecular structure that comprises a hydrophobic portion and a hydrophilic portion.

3. The assembly of claim 2, wherein the hydrophobic portion comprises a fluoropolymer repeat unit.

4. The assembly of claim 3, wherein the fluoropolymer comprises tetrafluoroethylene repeat units.

5. The assembly of claim 2, wherein the hydrophilic portion comprises a sulfonic acid group, a phosphonic acid group, or a sulfonamide acid group.

6. The assembly of claim 5, wherein the sulfonic acid group is a sulfonic acid group-terminated perfluorovinyl ether group.

7. The assembly of claim 1, wherein the ionic liquid has at least one complex grafted to the polymer.

8. The assembly of claim 1, wherein the ionic liquid comprises an imidazolium, pyridinium, tetralkylammonium, pyrrolidinium, trialkylsulfonium, pyrazolium, triazolium, thiazolium, oxazolium, pyridazinium, pyrimidinium, or pyrazinium cation.

9. The assembly of claim 8, wherein the ionic liquid comprises one or more anions selected from the group consisting of Cl, Br, $BF_4$, $PF_6$, $AlCl_4$, SCN, $HSO_4$, $HCO_3$, $CH_3SO_3$, $CH_3CH_2SO_4$, $(CH_3(CH_2)_3O)_2POO$, $(CF_3SO_2)_2N$, dicyanamide, $CF_3SO_3$, $(CF_3CF_2SO_2)_2N$, L-(+)-lactate, $CH_3SO_4$, and $CH_3COO$.

10. The assembly of claim 1, wherein the ionic liquid comprises one or more cations according to the formula:

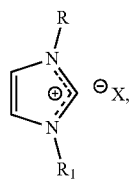

wherein R and R1 are independently H, substituted or unsubstituted alkyl of 1 to 30 carbon atoms, or substituted or unsubstituted aryl of 6 to 30 carbon atoms; and X is an anion.

11. The assembly of claim 10, wherein R is selected from the group consisting of $—(CH_2)_3CH_3$, $—CH_2CH_3$, $—CH_3$, $—CH=CH_2$, $—CH_2CN$, and $—(CH_2)_3CN$, and $R_1$ is selected from the group consisting of H, $—CH_3$, $—CH_2CN$, and $—(CH_2)_3CN$.

12. The assembly of claim 1, wherein either or both of the sensing electrode has an ionic liquid retained within the electrode.

13. The assembly of claim 1, wherein the membrane is a proton exchange membrane.

14. A membrane electrode assembly for a gas sensor, comprising
   a sensing electrode;
   a counter electrode; and
   a polymer membrane disposed between the sensing electrode and the counter electrode, the polymer membrane comprising an ionic liquid retained therein,
   wherein either or both of the sensing electrode and the reference electrode comprises carbon particles, an ionomer, an ionic liquid retained within the electrode, and optionally a catalyst.

15. A gas sensor comprising a housing having disposed therein a membrane electrode assembly comprising:
   a sensing electrode;
   a counter electrode; and
   a polymer membrane comprising an ionomer, disposed between the sensing electrode and the counter electrode, the polymer membrane comprising an ionic liquid retained therein;
   said housing containing a reference gas chamber to which the counter electrode is exposed, and a test gas chamber to which the sensing electrode is disposed;
   a pathway for test gas to enter the test gas chamber; and
   an electrical circuit connecting the sensing electrode and the counter electrode.

16. The gas sensor of claim 15 wherein the test gas is carbon monoxide.

17. The gas sensor of claim 16, the sensor being free of a liquid water reservoir.

18. A method of using the sensor of claim 15, comprising generating a difference in electronegative potential between the sensing electrode and the counter electrode that is responsive to the presence and/or concentration of a component in a gas being tested, measuring voltage or current in said electrical circuit, and converting the measured voltage or current to a reading indicative of the presence and/or concentration of the component in the gas being tested.

19. The method of claim 18, further comprising adjusting the conversion of measured voltage or current to the reading based on humidity.

20. The method of claim 19, wherein the humidity is determined based on the impedance or conductivity of the electrode assembly.

* * * * *